United States Patent
Lee et al.

(10) Patent No.: US 10,857,336 B2
(45) Date of Patent: Dec. 8, 2020

(54) IMPLANTABLE UROLOGICAL DEVICE WITH IMPROVED RETRIEVAL FEATURE

(71) Applicant: TARIS Biomedical LLC, Lexington, MA (US)

(72) Inventors: Heejin Lee, Arlington, MA (US); Hong Linh Ho Duc, Weston, MA (US)

(73) Assignee: TARIS Biomedical LLC, Lexington, MA (US)

( * ) Notice: Subject to any disclaimer, the term of this patent is extended or adjusted under 35 U.S.C. 154(b) by 1006 days.

(21) Appl. No.: 14/397,401

(22) PCT Filed: May 20, 2013

(86) PCT No.: PCT/US2013/041877
§ 371 (c)(1),
(2) Date: Oct. 27, 2014

(87) PCT Pub. No.: WO2013/177068
PCT Pub. Date: Nov. 28, 2013

(65) Prior Publication Data
US 2015/0088150 A1 Mar. 26, 2015

Related U.S. Application Data

(60) Provisional application No. 61/649,253, filed on May 19, 2012.

(51) Int. Cl.
*A61M 27/00* (2006.01)
*A61L 31/16* (2006.01)
(Continued)

(52) U.S. Cl.
CPC ......... *A61M 27/008* (2013.01); *A61L 31/022* (2013.01); *A61L 31/043* (2013.01);
(Continued)

(58) Field of Classification Search
CPC .............. A61M 27/008; A61M 31/002; A61M 25/0017; A61M 2210/1089; A61L 31/043;
(Continued)

(56) References Cited

U.S. PATENT DOCUMENTS 4,790,809 A * 12/1988 Kuntz ............... A61M 25/0045
600/434
5,019,102 A * 5/1991 Hoene ............... A61M 25/0069
604/264
(Continued)

FOREIGN PATENT DOCUMENTS

| WO | 9958083 A1 | 11/1999 | |
|---|---|---|---|
| WO | 2008036711 A1 | 3/2008 | |
| WO | WO 2008036711 A1 * | 3/2008 | .......... A61M 27/002 |

OTHER PUBLICATIONS

International Search Report and the Written Opinion for PCT/US2013/041877 dated Oct. 22, 2013.
(Continued)

*Primary Examiner* — Suba Ganesan
*Assistant Examiner* — Aren Patel
(74) *Attorney, Agent, or Firm* — Eversheds Sutherland (US) LLP

(57) ABSTRACT

A urological medical device having a retrieval string is provided. The retrieval string has a proximal end connected the device and an opposed distal end. In a first embodiment, the retrieval string is configured in an initial confined form which, following a period of deployment in a patient's bladder, changes to an unconfined form in which the distal end of the retrieval string is extendible into the urethra to enable extraction of the device from bladder by pulling the retrieval string. The device may include a bioerodible component which permits the retrieval string to take the unconfined form following degradation of the bioerodible component in vivo. In another embodiment, the retrieval string
(Continued)

includes a ferromagnetic material, which can be magnetically captured to facilitate removal of the device from the bladder. The ferromagnetic retrieval string may be buoyant in urine.

28 Claims, 7 Drawing Sheets

(51) Int. Cl.
    *A61M 25/00* (2006.01)
    *A61M 31/00* (2006.01)
    *A61L 31/18* (2006.01)
    *A61L 31/14* (2006.01)
    *A61L 31/02* (2006.01)
    *A61L 31/04* (2006.01)
    *A61L 31/06* (2006.01)
    *A61K 9/00* (2006.01)
    *A61B 17/50* (2006.01)

(52) U.S. Cl.
    CPC .............. *A61L 31/06* (2013.01); *A61L 31/148* (2013.01); *A61L 31/16* (2013.01); *A61L 31/18* (2013.01); *A61M 25/0017* (2013.01); *A61M 31/002* (2013.01); *A61B 17/50* (2013.01); *A61K 9/0036* (2013.01); *A61L 2300/402* (2013.01); *A61L 2400/16* (2013.01); *A61M 2210/1089* (2013.01)

(58) Field of Classification Search
    CPC ...... A61L 31/06; A61L 31/022; A61L 31/148; A61L 31/16; A61L 31/18; A61L 2300/402; A61L 2400/16; A61F 13/15; A61F 13/20; A61F 2002/047; A61F 13/34
    USPC ...................................................... 623/23.66
    See application file for complete search history.

(56) References Cited

U.S. PATENT DOCUMENTS

| | | | |
|---|---|---|---|
| 5,599,291 A | 2/1997 | Balbierz et al. | |
| 5,629,008 A | 5/1997 | Lee | |
| 6,171,298 B1 | 1/2001 | Matsuura et al. | |
| 6,524,608 B2 | 2/2003 | Ottoboni et al. | |
| 6,652,569 B1 * | 11/2003 | Taylor | A61F 2/04 606/108 |
| 6,656,146 B1 * | 12/2003 | Clayman | A61M 27/008 604/544 |
| 8,690,840 B2 | 4/2014 | Lee et al. | |
| 8,801,694 B2 | 8/2014 | Lee et al. | |
| 9,017,312 B2 | 4/2015 | Lee et al. | |
| 9,107,816 B2 | 8/2015 | Lee et al. | |
| 2004/0059279 A1 | 3/2004 | McWeeney et al. | |
| 2004/0260272 A1 | 12/2004 | Friedman et al. | |
| 2006/0282159 A1 * | 12/2006 | Taheri | A61B 17/12022 623/1.38 |
| 2007/0255222 A1 | 11/2007 | Li et al. | |
| 2008/0004578 A1 * | 1/2008 | Hixon | A61L 31/148 604/326 |
| 2009/0149833 A1 * | 6/2009 | Cima | A61K 9/0024 604/517 |
| 2010/0331770 A1 | 12/2010 | Lee et al. | |
| 2011/0052497 A1 | 3/2011 | Lee | |
| 2011/0152839 A1 | 6/2011 | Cima et al. | |
| 2011/0218488 A1 | 9/2011 | Boyko et al. | |
| 2013/0131637 A1 | 5/2013 | DiCesare et al. | |
| 2013/0158675 A1 | 6/2013 | Hutchins, III et al. | |
| 2013/0324946 A1 | 12/2013 | Tobias et al. | |

OTHER PUBLICATIONS

Birch, et al., "Tethered Ureteric Stents—A Clinical Assessment" British J. Urology, 62:409-11 (1988).
Campell et al., "Exchange Ureteral Stent Insertion Using Pullout Suture After Extracorporeal Shock-Wave Lithotripsy" Urology, vol. XXIX, No. 6 (Jun. 1987).
Jones J.S., "Shortened Pull-String Simplifies Office-Based Ureteral Stent Removal" Urology 60(6): 1095-97 (2002).

* cited by examiner

IMPLANTABLE UROLOGICAL DEVICE
WITH IMPROVED RETRIEVAL FEATURE

CROSS-REFERENCE TO RELATED APPLICATIONS

This patent application claims the benefit of U.S. Provisional Patent Application No. 61/649,253, filed May 19, 2012, which is incorporated herein by reference in its entirety.

BACKGROUND

Ureteral stents and other medical devices, such as the intravesical drug delivery devices described in U.S. Patent Application Publication No. 2011/0152839 to Cima et al., may be provided with a retrieval string to facilitate removal of the device from the patient. The retrieval string may be called a tether, dangler, dangler string, retrieval ligature, withdrawal string, pull string, pull-string suture, or pullout suture. Ideally, the retrieval string enables the patient or physician to remove the device from the patient's ureter, through the bladder and urethra, without the need for a cystoscopic procedure.

The retrieval string generally must extend through and outside of the patient's urethra the entire period the device is deployed in the patient in order for the patient or medical professional to be able to grasp the string. However, this may cause other problems. For example, the patient may accidentally tug on the string, e.g., during or following urination, which may cause pain if the stent is shifted in the ureter. It also could cause the device to be dislodged or excreted prematurely. In addition, the retrieval string may be uncomfortable to the patient, may interfere with directing the flow of urine during urination, and/or may increase the risk of infection by providing a pathway for bacteria migration.

U.S. Pat. No. 6,258,098 to Taylor et al. discloses a magnetic system to blindly retrieve ureteral stents. A ferromagnetic bead is tethered to the proximal end of a ureteral stent with a flaccid string. When the stent is introduced, the bead hangs from the stent in the bladder. Retrieval is performed by introducing a catheter into the bladder tipped with a rare-earth magnet, which has a very strong magnetic field. The magnet attracts the bead, and exerts sufficient force on the bead to pull the stent out through the ureter and urethra when the catheter is withdrawn. U.S. Pat. No. 4,790,809 to Kuntz also discloses a system in which a ferromagnetic element is incorporated into the tip of a ureteral stent. These systems are all geared towards retrieving stents, which are confined in their deployment locations. In contrast, a free-floating intravesical device would not likely be useful or readily adaptable for use with those magnetic systems. For example, a free-floating device may be located anywhere within the bladder and perhaps in any orientation, making a blind search for the ferromagnetic tip much more difficult than one such as the stent which generally would be in a known location and orientation even without cystoscopic visualization. Moreover, the addition of such large ferromagnetic elements as disclosed in those patents might cause an unsecured device to sink to the bladder neck and increase the risk of prematurely entraining the ferromagnetic element in the urethra and accidentally voiding the device from the bladder.

It therefore would be desirable to provide devices and methods which facilitate the selective retrieval of deployed urological devices from a patient, while avoiding one or more of the drawbacks associated with conventional retrieval strings and designs.

BRIEF SUMMARY

Improved systems and methods for retrieving medical devices from the bladder are provided. In one aspect, the system includes a urological device configured for controlled emergence of one or more retrieval strings attached to the urological device. In one embodiment, the retrieval string has a proximal end connected the urological device and an opposed distal end and is configured in an initial confined form which, following a period of deployment of the medical device in a urinary bladder of a patient, changes to an unconfined form in which the distal end of the at least one retrieval string is extendible into the urethra of the bladder to enable extraction of the medical device from bladder by pulling the at least one retrieval string. In one particular embodiment, the device further includes a bioerodible component operable to (i) maintain the at least one retrieval string in its initial confined form, and (ii) permit the at least one retrieval string to take the unconfined form following degradation of the bioerodible component in vivo. Also in particular embodiments, the system includes a hydrodynamic cap on the distal end of the retrieval string to facilitate entry into and passage through the urethra, to facilitate emergence of the distal end of the retrieval string from the bladder.

In another aspect, the system includes a urological device with a retrieval string that includes a ferromagnetic material effective to facilitate magnetic capture of the retrieval string, such as by magnetic coupling with a magnet-tipped catheter inserted through the urethra of the patient. In a particular embodiment, the ferromagnetic retrieval string is buoyant in urine within the bladder. The ferromagnetic retrieval string may or may not be configured to have an initial confined form which, following a period of deployment of the medical device in a urinary bladder of a patient, changes to an unconfined form as described above.

In embodiments, the urological device incorporating one or a combination of these systems is a drug delivery device. In a particular embodiment, the urological device includes (i) a device body having at least one drug reservoir lumen, and (ii) a drug formulation positioned in the at least one drug reservoir lumen, wherein the device is elastically deformable between a retention shape for retaining the urological device in the bladder and a low profile shape for deployment of the urological device through a patient's urethra. In an embodiment, the urological device is configured to permit the distal end of the retrieval string in its unconfined form to extend out from the urethra of the bladder when the device is in its retention shape and thereby enable the patient or a physician to pull the distal end of the retrieval string and cause the device to take its low profile shape, permitting the device to be extracted through the patient's urethra.

DETAILED DESCRIPTION

Figure 1:
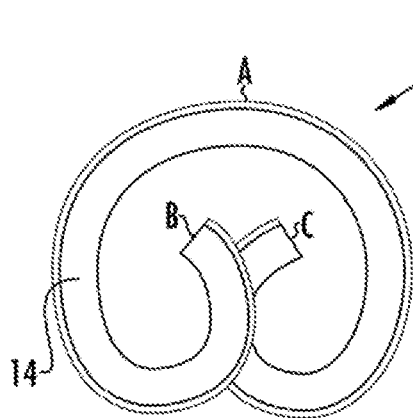
FIG. 1 is a plan view of a prior art urological device which may be modified to include embodiments of the retrieval systems described herein.

Improved urological devices and methods for device retrieval from patients are provided. The devices and method advantageously include one or more retrieval features that enable the devices to be removed from the patient without cystoscopy, a procedure which patients strongly wish to avoid.

In a preferred embodiment, the devices provide controlled emergence of the retrieval string from urethra, such that removal can be performed at home by the patient or by a medical professional in a simple out-patient (office) procedure. In another embodiment, the device includes a buoyant, magnetic retrieval string that can be magnetically coupled to the end of catheter inserted through the urethra in a blind procedure to pull the retrieval string into and through the urethra, so that the retrieval string can used to remove the device from patient, again such that the removal can be performed by a medical professional in a simple out-patient (office) procedure without cystoscopy.

The urological device can be essentially any device that is designed for temporary therapeutic or diagnostic use in a patient's urinary tract and urogenital system. Non-limiting examples includes ureteral stents, drug delivery devices, or combinations thereof. In a preferred embodiment, the urological device is one of the devices described in U.S. Patent Application Publication No. 2011/0152839 to Cima et al.; PCT Application Publication WO 2012/019155 to Taxis Biomedical, Inc., et al.; U.S. Patent Application Publication No. 2012/0089122 to Lee et al., PCT Application Publication WO 2012/018923 to Taxis Biomedical, Inc., et al.; U.S. Patent Application Publication No. 2010/0331770 to Lee, et al.; and U.S. Patent Application Publication No. 2011/0060309 to Lee, et al., which are incorporated herein by reference.

The retrieval string may be constructed of any suitable material, and may include natural or synthetic fibers. The retrieval string may be of monofilament or multifilament (e.g., braided, spun, twisted, or the like) construction. Monofilament string may be preferred, as it may reduce bacterial growth due to its smooth surface. It preferably is flaccid and has a relatively thin diameter to minimize patient discomfort, but with high enough tensile strength to resist breaking when being pulled to withdraw the attached medical device from the patient. In embodiments, the retrieval string comprises a material selected from those known in the art for use in/as non-absorbable sutures. Examples of such materials of construction for such sutures include Nylon 6, polypropylene, silk, cotton, polyester, polyester/Dacron, 316 stainless steel, and polymer blends, such as poly(vinylidene fluoride) with poly(vinylidene fluoride-co-hexafluoropolypropylene), among others. The retrieval string may be dyed, clear or have its natural color. The retrieval string may be coated and/or impregnated with an antimicrobial agent known in the art. The retrieval string may be attached to the urological device through a variety of means, including adhesive bonding, tying the string through or around part of the device, or the like.

The retrieval string may be a single string or a loop. As used herein, the terms "end portion" or "distal end" in reference to a portion of the retrieval string can be either a single strand or a loop.

The devices and methods disclosed herein may be used in humans, whether male or female, adult or child, or in other mammals, such as for veterinary or livestock applications. Accordingly, the term "patient" as used herein may refer to humans or other mammals.

The devices and methods can be understood with reference to FIGS. 1-15, which are exemplary and not limiting. The drawings are not to scale.

In a first type of embodiment (Type 1), the device includes a long retrieval string, such that after the urological device is inserted into the patient, an end portion of the retrieval string is in a position extending outside of the patient's urethra. The other end portion of the retrieval string may be attached to the urological device at various locations depending on the device type and the deployed location of the urological device in the patient. The string can be a single strand or a loop style.

Figure 2:
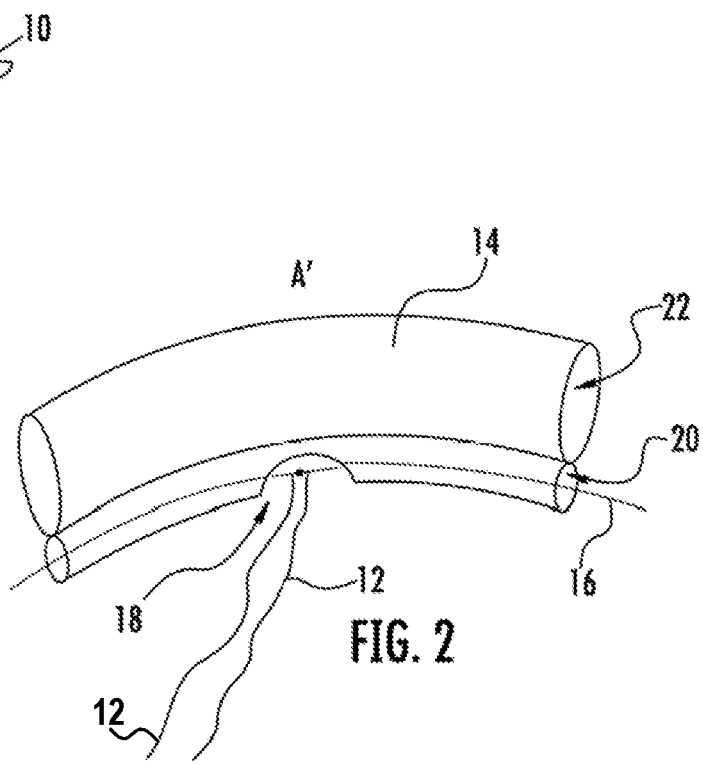
FIG. 2 is a plan view of one embodiment of an intravesical drug delivery device having a retrieval string attached thereto.

FIG. 1 shows one example of a urological device, an elastically deformable drug delivery device 10, which is described in U.S. Patent Application Publication No. 2012/0089122 to Lee et al. The attachment position of the retrieval string can be varied, such as in the middle portion (shown as "A" in FIG. 1) or at either end (shown as "B" and "C" in FIG. 1) of the body 14 of device 10. It may be sutured to the device 10. In one embodiment which is shown in FIG. 2, the retrieval string is attached to the wire form 16 (i.e., the retention frame) through an opening 18 in the side wall of the retention frame lumen 20 adjacent to the drug reservoir lumen 22, which initially would house a drug payload (not shown). The retrieval string 12 may be tied or knotted to or wrapped around the wire form 16.

In other embodiments, the retrieval string 12 is attached at one of the end portions (B and C in FIG. 1) of device 10. In embodiments, one or both of the ends of the drug reservoir lumen 22 are closed off with an end piece, which may be or may include a plug secured within the end opening of the drug reservoir lumen. The end piece may be made of essentially any biocompatible material. An example material of construction is silicone, although other biocompatible polymers and materials can be used.

Figure 3A:
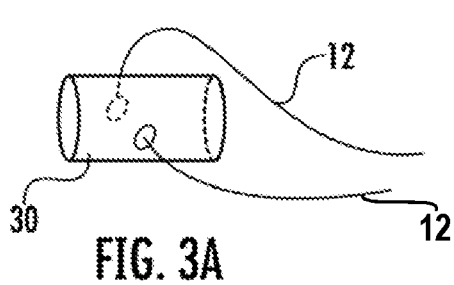
FIGS. 3A-3D are perspective views showing various embodiments for attaching a retrieval string to end pieces of one type of an intravesical drug delivery device.
Figure 3B:
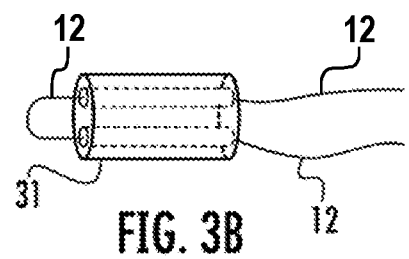
Figure 3C:
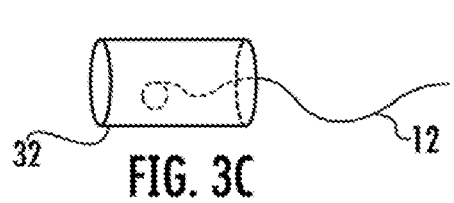
Figure 3D:
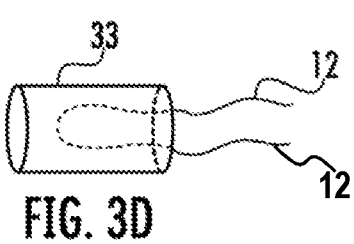
Figure 3E:
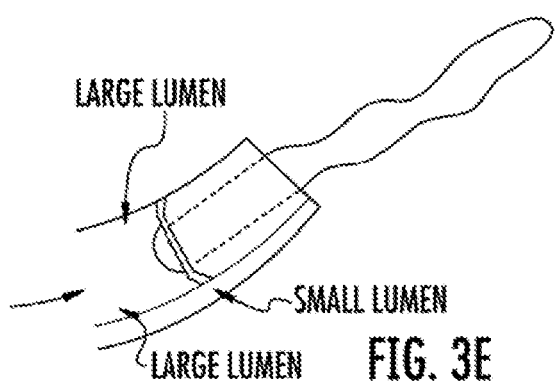
FIG. 3E shows a cross-sectional view of an end piece, with a retrieval string, installed in a lumen of a tubular body of one embodiment of an intravesical drug delivery device.
Figure 4:
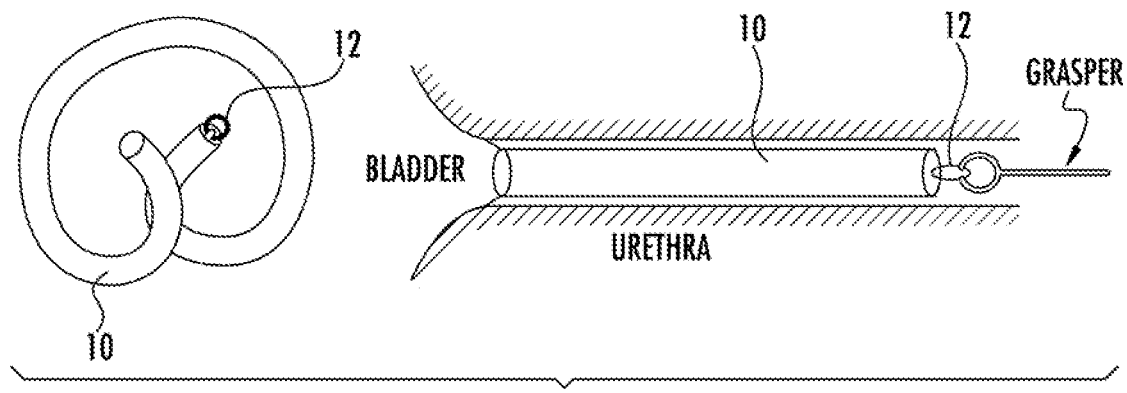
FIG. 4 shows one embodiment of a drug delivery device having a short retrieval string attached to an end of a drug delivery device in a retention shape and in a low profile shape for pulling the device through a patient's urethra.

The retrieval string may be knotted and looped through an aperture in the end piece or other portion of the urological device. Alternatively, the retrieval string may be potted in the end piece or other portion of the urological device, FIGS. 3A-3D shows four possible embodiments in which a retrieval string 12 is attached to an end piece 30, 31, 32, or 33. FIG. 3A shows an end piece 30, which has a single hole, traverse to the longitudinal axis of the end piece and through which retrieval string 12 is threaded. FIG. 3B shows an end piece 31, which has two holes parallel to the longitudinal axis of the end piece and through which the retrieval string 12 is threaded. FIG. 3C shows an end piece 32, in which the proximal end portion of the retrieval string 12 is embedded, e.g., potted, with the distal end portion extending out of the end piece. In FIG. 3D, a mid-portion of a string is embedded in end piece 33, such that the two retrieval strings 12 extend from end piece 33. FIG. 3E shows an end piece component inserted into the end of the large lumen of the drug delivery device housing.

The Type 1 embodiment, described above, may not be preferred. That is, although having the retrieval string placed outside the urethra is useful to aid in non-cystoscopic device retrieval, it comes with the potential for discomfort, infection risk, inadvertent/premature withdrawal of a device, and urinary spraying or problems with the direction of the urinary stream. To overcome these disadvantages, additional types of device embodiments are provided, as detailed below.

In a second type embodiment (Type 2), the end portion of the retrieval string (which may be in the form of a loop) is free but does not extend outside the urethra. Therefore, the end portion of the retrieval sting must be grasped by a medical profession in a minimally invasive procedure, which may be blind (no visualization of the device or retrieval string) or visualized with a cystoscope. In one sub-type, the retrieval string is short compared with Type 1. The device in FIG. 4, for example, can be retrieved in a linear fashion during cystoscopic retrieval when the string was grasped. Retrieval in a linear fashion can reduce the possible discomfort of patients when the device passes through the urethra. In a second sub-type, the retrieval string is magnetic, and preferably buoyant, and can be readily grasped and withdrawn in a blind procedure.

In a third type embodiment (Type 3), all or a portion (such as the end portion) of the retrieval string is wound, coiled, encapsulated, and/or otherwise confined in or on the device (i.e., it is not free and does not extend from the urethra) until such time that device retrieval is desired. That is, the device is designed to provide controlled emergence of the retrieval string from the urethra.

Figure 5:
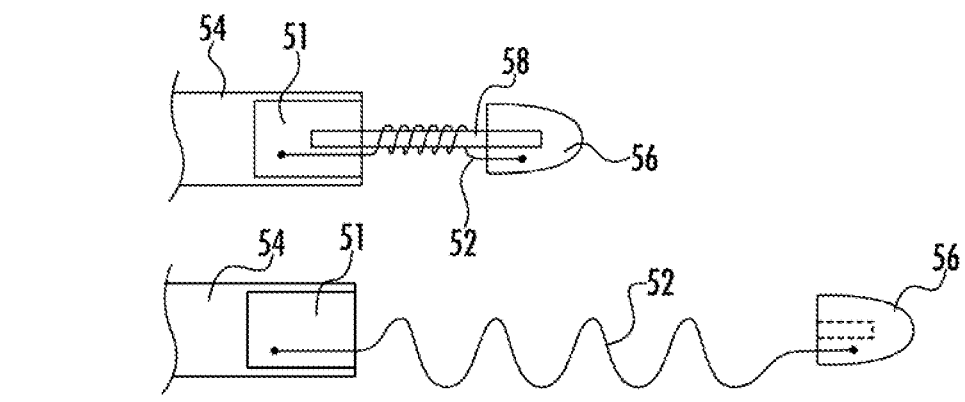
FIG. 5 is a plan view of one embodiment of a urological device having a rod shaped bioerodible component with a retrieval string (and hydrodynamic cap) wound thereabout, for providing controlled emergence of the retrieval string.

One embodiment of a Type 3 device is shown in FIG. 5. Here, the urological device body 54 includes an end piece 51, and the retrieval string 52 is in a confined form, wound around a rod-shaped bioerodible component 58. The proximal end of the retrieval string 52 is attached to end piece 51, and the distal end of the retrieval string is attached to a hydrodynamic cap 56. Following deployment of the device in the patient, the bioerodible component 58 degrades. Once the bioerodible component 58 loses sufficient integrity to connect the hydrodynamic cap 56 and the urological device body 54 after a pre-determined period, the retrieval string 52 becomes unconfined, e.g., unwound, as shown in the lower illustration of FIG. 5. Then, the hydrodynamic cap 56 can become entrained in the patient's urethra. Once the hydrodynamic cap 56 is entrained in the urethra, hydrodynamic force applied to the cap 56 during urination will drag the hydrodynamic cap 56 and the distal end portion of the retrieval string 52 out of the urethra, where it can be readily grasped, thereby enabling the patient or caregiver to pull the urological device and withdraw it from the patient's body.

As used herein, the terms "bioerodible" or "biodegradable" means that the device or a component thereof (e.g., the bioerodible component associated with release of the retrieval string) degrades in vivo by dissolution, enzymatic hydrolysis, erosion, resorption, or a combination thereof. In one embodiment, this degradation occurs at a time that does not interfere with the intended kinetics of release of the drug from the device. For example, substantial erosion of the bioerodible portion may not occur until after the drug formulation is substantially or completely released.

In a preferred embodiment, the hydrodynamic cap 56 is constructed to be non-buoyant (after the bioerodible component has failed) so that it will sink within the bladder, facilitating its entrainment with urine flowing into/through the urethra. For example, the hydrodynamic cap may be formed of a biocompatible polymer, metal, or combination thereof, such that the cap has a density greater than about 1.0 g/mL.

The hydrodynamic cap 56 can have essentially any suitable shape. In embodiments, it is less than 5 mm in its longest dimension. The shape may be cylindrical, bullet-shaped, bulbous, elliptical, circular, bow-shaped, spherical, ellipsoid, crescent, half-ring, bean-shaped, banana-shaped, doughnut-shaped, or rectangular. Other shapes are envisioned. The hydrodynamic cap may be made of any suitable biocompatible material.

The hydrodynamic cap is optional, and the variations of the urological device providing controlled emergence of the retrieval string without a hydrodynamic cap are envisioned. For example, the retrieval string itself may be sufficiently non-buoyant and/or shaped at the distal end portion to promote urinary entrainment.

Figure 7:
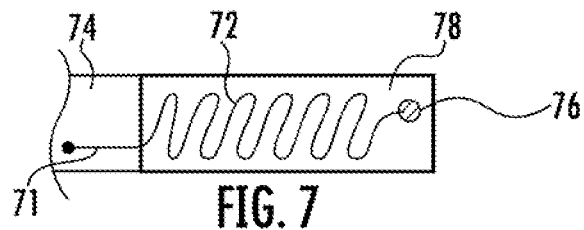
FIG. 7 is a plan view of one embodiment of a urological device having a bioerodible component with an embedded retrieval string and a hydrodynamic cap, for providing controlled emergence of the retrieval string.

In another of a Type 3 device embodiment, the retrieval string in the confined form is embedded or housed in a bioerodible component. For example, as shown in FIG. 7, device body 74 includes a retrieval string 72 with a hydrodynamic cap 76, which are embedded in a bioerodible component 78, except for a proximal end portion 71 of the retrieval string 72, which is used to secure the retrieval string to the urological device body 74. Following a selected period of device deployment in the bladder, the bioerodible component will degrade and permit the retrieval string 72 and hydrodynamic cap 76 to take a free, unconfined form, which can then pass with urine through the urethra to facilitate device withdrawal from the patient.

Figure 8:
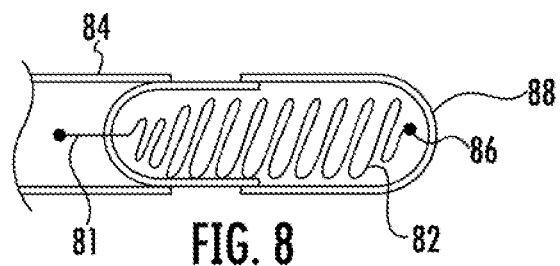
FIG. 8 is a plan view of one embodiment of a urological device having a bioerodible capsule containing a retrieval string and a hydrodynamic cap, for providing controlled emergence of the retrieval string.

Another Type 3 device embodiment is shown in FIG. 8. Here, device body 84 includes a retrieval string 82 with a hydrodynamic cap 86, which are confined in a bioerodible capsule 88, except for a proximal end portion 81 of the retrieval string 82, which is used to secure the retrieval string to the urological device body 84. Following a selected period of device deployment in the bladder, the bioerodible capsule will degrade and rupture, permitting the retrieval string 82 and hydrodynamic cap 86 to take a free, unconfined form, which can then pass with urine through the urethra to facilitate device withdrawal from the patient. In one embodiment, air (or another biocompatible gas) is provided in the bioerodible capsule 88 with the retrieval string 82 which advantageously may be used to promote buoyancy of the whole device in the bladder until the bioerodible capsule 82 degrades and is ruptured to release the string, the hydrodynamic cap, and the air.

Since the retrieval string in the foregoing embodiments will likely undergo a large strain in its confined position (e.g., when wound or contained in a small space), the retrieval string, in a preferred embodiment, consists of a thin silk or braided polyester suture material, rather than a monofilament nylon or monofilament polypropylene suture material.

Figure 9:
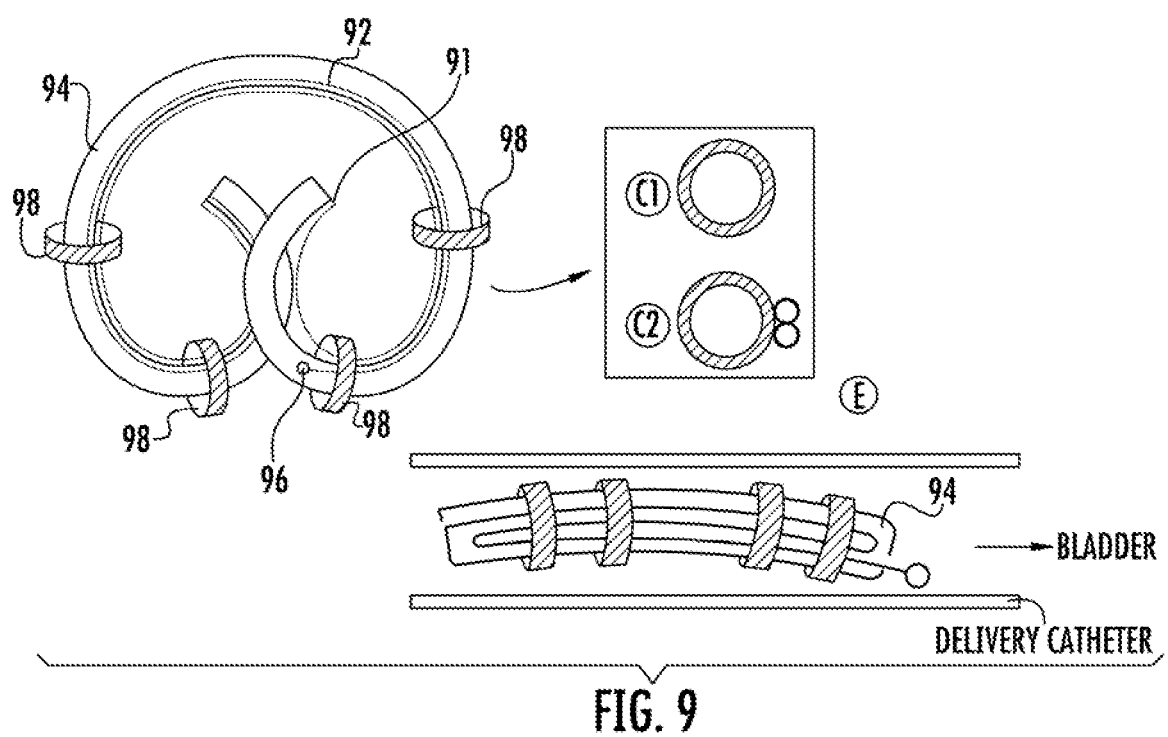
FIG. 9 shows plan views of one embodiment of a urological device having a retrieval string with a hydrodynamic cap confined in a folded position along an outer surface of the device body with a plurality of annular shaped bioerodible components, for providing controlled emergence of the retrieval string.

Yet another embodiment of a Type 3 device is shown in FIG. 9. Here, device body 94 includes a retrieval string 92 with a hydrodynamic cap 96. The proximal end 91 of the retrieval string is secured to an end of the device body, which may be a drug delivery device. The remainder of the retrieval string 92 is folded and constrained along the length of the device with four bioerodible components 98. Fewer or more bioerodible components may be used, depending for example on the particular shapes and dimensions of the device body and the bioerodible component(s). Following a selected period of device deployment in the bladder, the bioerodible components will degrade, permitting the retrieval string 92 and hydrodynamic cap 96 to take a free, unconfined form, which can then pass with urine through the urethra to facilitate device withdrawal from the patient. In this embodiment, the string 92 may be under relatively low strain, and so a monofilament suture material may be preferable. The number and shape and placement of the bioerodible components 98 can vary. The hydrodynamic cap is optional.

FIG. 9 also shows in a plan view that the bioerodible components 98 may be single- or multiple-lumen type. For the single lumen type, both the device body and the retrieval string may pass through the single lumen (C1). For the multiple lumen type, the device body may pass through the large lumen and the retrieval string may pass through either large or small lumens. The device 94 may be elastically deformable between a retention shape, shown in the upper illustration, for retaining the urological device in the bladder and a low profile shape for deployment of the urological device through a patient's urethra. This lower profile shape in a deployment catheter or cystoscope is shown in the lower illustration in FIG. 9.

Figure 6A:
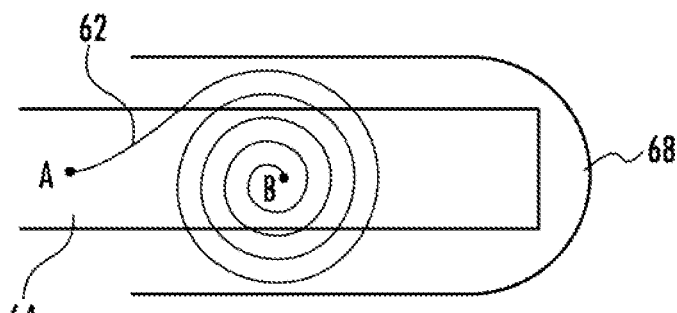
FIG. 6A is a plan view of one embodiment of a urological device having a coiled retrieval string (and hydrodynamic cap) covered by a bioerodible cap, for providing controlled emergence of the retrieval string.

The configuration in which the retrieval string is confined can impact the reliability, timing and ease with which the retrieval string is deployed following degradation of the bioerodible component. For example, the string should be able to be easily uncoiled without entanglement with itself or the urological device. FIG. 6A shows yet another embodiment of a Type 3 device. Here, the retrieval string 62 is spirally wound and confined inside a bioerodible cap 68. End A of the retrieval string is attached to urological device 64, while end B of the retrieval string is free. Once the bioerodible cap dissolves or degrades in urine, the retrieval string 62 will be uncoiled.

Figure 6B:
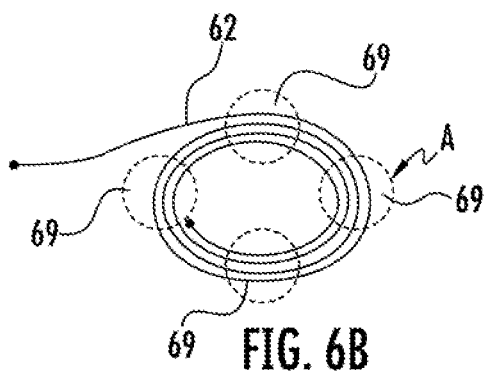
FIG. 6B is a plan view of one embodiment of a coiled retrieval string secured in a coiled configuration by a plurality of regions of bioerodible tacky material applied onto the coil.

In another embodiment, the bioerodible component may be in the form of a biodegradable and temporarily sticky material, which can be used in the process of forming the retrieval string into a confined structure. For example, a viscous polysaccharide aqueous solution can be used to facilitate the string coiling process, as shown in FIG. 6B. Here, the sticky material 69 is applied to only limited areas of the coil of retrieval string 62 as shown in FIG. 6B. Alternatively, the material or can be applied along all or substantially all of the string, before or after the string is folded or coiled into a confined form. The string tends to be straight locally or globally depending on its material and thickness. The sticky material remains sticky during the string coiling process and can become dry or solidified after the coiling process.

In another Type 2 device embodiment, the retrieval string is, or includes, a magnetic or ferromagnetic buoyant string. By making the string buoyant in urine, it may reduce or avoid having the string rest at the bottom of the bladder, potentially being dragged out by hydrodynamic forces during urination, which in turn may trigger discomfort to the patient, infection, possible anchoring of the device at the bladder neck, which could cause inflammation due to constant contact with the bladder wall. In one embodiment, the retrieval string—and advantageously only the retrieval string—is magnetically coupled to a magnet-tipped catheter. Once the string is out, it can be grasped by the patient or care provider to pull the device out completely out of the patient.

It is noted that the magnetic force necessary to pull out a string through the urethra generally is much lower than that needed to pull out a device directly. Consequently, the size of the ferromagnetic element needed to obtain the required magnetic force for retrieval is also smaller. This enables a reduction in the size of the ferromagnetic element while still retaining enough magnetic attraction with a magnet to retrieve the string.

Furthermore, in a preferred embodiment, the magnetic component associated with the retrieval string is spread over a substantial portion of the retrieval string, not just at its end, which advantageously increases the likelihood and ease of magnetically coupling the string to a magnet-tipped catheter in a blind procedure (since the ferromagnetic elements/string will be scattered in more locations throughout the bladder), as compared to a blind procedure in which only the tip end of the retrieval string or urological device is magnetic.

Figure 10:
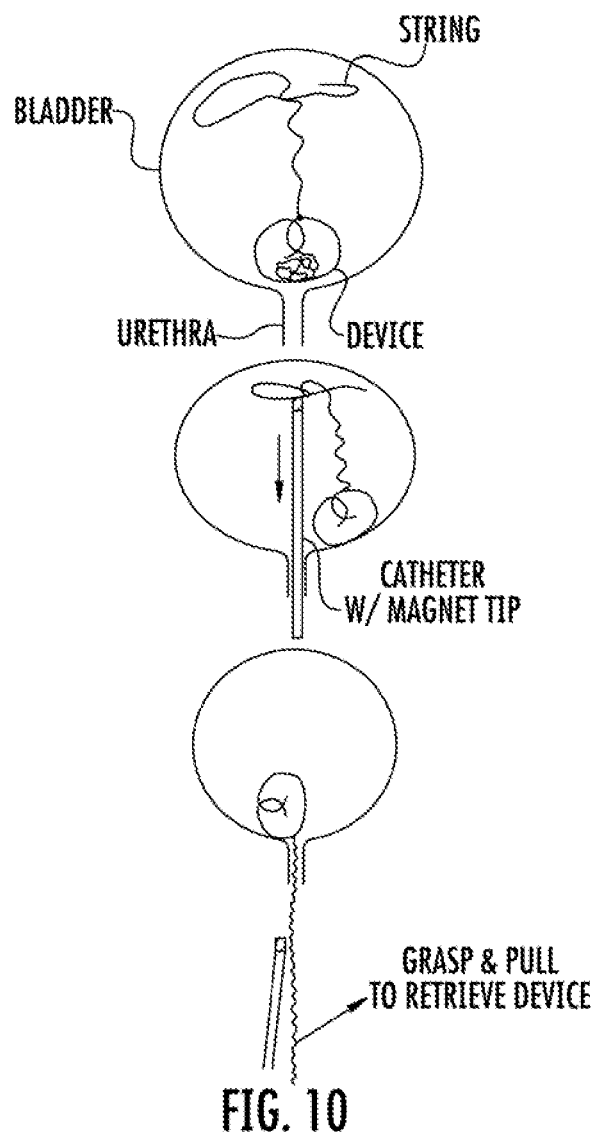
FIG. 10 shows a sequence of steps for retrieval of a urological device from the bladder using one embodiment of a retrieval system that includes a ferromagnetic retrieval string and magnet-tipped catheter device.

FIG. 10 shows a sequence of illustrations showing how the retrieval process works in one embodiment. In the first (top) illustration, the urological device, such as a drug delivery device, sits in the bottom of the bladder, while the buoyant retrieval string floats toward the top of the bladder, staying out of the area near the bladder neck where it might get dragged out through the urethra. In the second illustration, a magnet-tipped catheter is inserted into the bladder through the urethra, and the magnet becomes magnetically coupled to the retrieval string which contains a ferromagnetic material. Then, the magnet-tipped catheter and part of the coupled retrieval string are withdrawn from the bladder. Lastly, the string is exteriorized through the urethra and pulled to retrieve the device from the bladder through the urethra.

Figure 11:
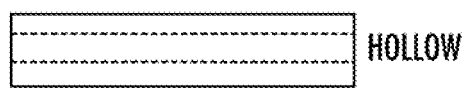
FIG. 11 shows two possible constructions of the retrieval strings described herein.
Figure 11:
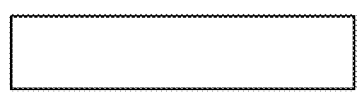

FIG. 11 shows two types of retrieval string constructions. In the top portion of the Figure, the string is hollow. That is, annular in shape, with a lumen that can be loaded with one, or preferably, multiple ferromagnetic elements (not shown) that are dimensioned to fit into the lumen. In the bottom portion of the Figure, the string is solid. It has no lumen. In such embodiments, the ferromagnetic elements may be dispersed in the material forming the string. For example, the string may be formed of a synthetic polymer, which is melted and then extruded into one or more filaments. The ferromagnetic material may be mixed/dispersed into the melt prior to extrusion.

Figure 12:
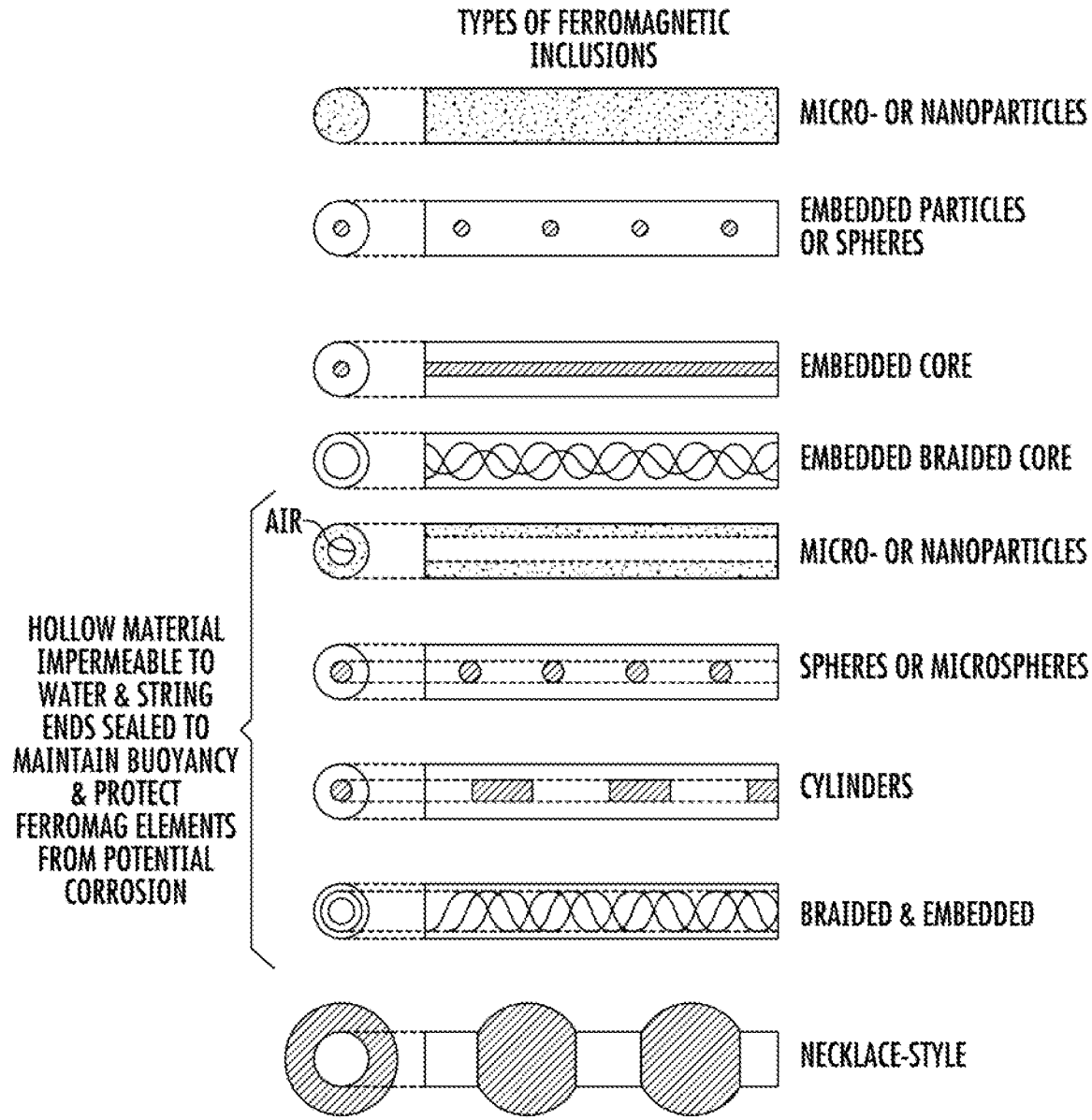
FIG. 12 shows several possible constructions of retrieval strings that include a ferromagnetic material for use with the retrieval systems described herein.

FIG. 12 shows a number of potential configurations of the string with ferromagnetic elements. The configuration chosen for implementation may depend on how much force is actually necessary to pull the string out of the urethra, and what configurations meet this requirement. The ferromagnetic elements do not necessarily need to be placed along the whole length of the string. For example, they could be along only part of the string if one wants to make sure that a specific part of the string is attached to the magnet.

The controlled emergence retrieval string or the magnetic buoyant retrieval string systems described herein may be used with essentially any type of fixed or free-floating medical device that is deployed in or through the urinary bladder of a patient. Particular, non-limiting examples include ureteral stents and intravesical drug delivery devices, such as untethered, or free-floating, drug delivery devices. In another embodiment, the urological device may be a diagnostic or imaging device, such as disclosed in U.S. Patent No. 2010/0076261 to Neeman et al. In one embodiment, the magnetic buoyant retrieval string is configured for controlled emergence.

Figure 14:
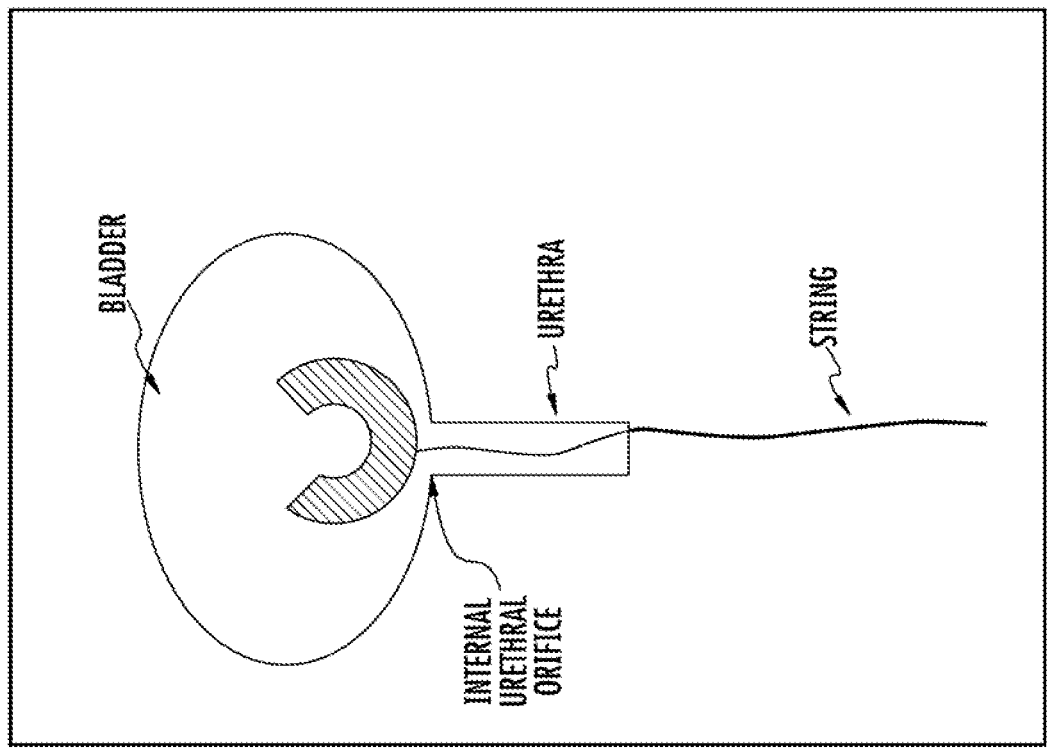

The location where the retrieval string is attached to the urological device may affect the removal force. For example, with embodiments of the intravesical drug delivery device, if the string is attached in the middle portion (as in FIG. 14) or at least the location where the device can 'bridge' across the internal urethral orifice, more force (to buckle the device) will be required to introduce the device to the urethra compared with the case where the string is attached to the end of the device or where the device does not bridge across the urethral orifice (as in FIG. 15). The embodiment of FIG. 14 is preferable in the case where the string is present out of the urethra during the whole treatment period to prevent accidental pull-out of the device.

The retrieval string systems described above may be used with a variety of implantable urological devices. Additional description of embodiments of such devices is provided hereinbelow.

In one embodiment, the urological device is a drug delivery device designed for insertion through the urethra and free-floating retention in the bladder. In one embodiment, the device includes a drug reservoir portion, a retention frame portion, and a retrieval string portion. The device has a relatively expanded shape suited for retention in the bladder, but can be elastically compressed to take a relatively lower-profile shape for deployment through the channel of a deployment instrument, such as a cystoscope or catheter. Following deployment into the (i.e. release into the bladder), the device may assume the relatively expanded shape to retain the drug delivery device.

In another embodiment, the urological device is ureteral stent device which includes a retrieval string portion at or near the bladder-residing end of the stent. In one embodiment, the ureteral stent device also includes at least one drug delivery portion associated with the ureteral stent portion, such as with one of the stent ends. In particular embodiments, the drug delivery portion is positioned on the bladder-residing end to deliver drug locally to the bladder, although the kidney-residing end also may be associated with a drug delivery portion, or both ends may be associated with separate drug delivery components, regardless of whether the stent ends are straight or pigtailed. The drug delivery portion also may extend along all or some of the central body of the ureteral stent portion in some embodiments.

For the purposes of this disclosure, terms such as "relatively expanded shape," "relatively higher-profile shape," or "retention shape" generally denote any shape suited for retaining the device in the intended implantation location, including but not limited to a coiled or pretzel shape that is suited for retaining the device in the bladder. Similarly, terms such as "relatively lower-profile shape," "low-profile shape," or "deployment shape" generally denote any shape suited for deploying the drug delivery device into the body, including the linear or elongated shape that is suited for deploying the device through the working channel of a catheter, cystoscope, or other deployment instrument positioned in a lumen of the body, such as the urethra. In embodiments, the drug delivery device may naturally assume the relatively expanded shape and may be deformed, either manually or with the aid of an external apparatus, into the relatively lower-profile shape for insertion into the body. Once deployed, the device may spontaneously or naturally return to the initial, relatively expanded shape for retention in the body.

In one embodiment, the drug delivery device includes a tube or wall that defines a drug reservoir lumen and a tube or wall that defines a retention frame lumen. A drug formulation, which may comprise one or more solid drug units (e.g., tablets or capsules) including one or more drugs, may be contained in the drug reservoir lumen. End plugs may close the ends of the drug reservoir lumen and/or the retention frame lumen. In one embodiment, the retrieval string may be operable associated with one or both ends of the device. In another embodiment, the retrieval string may be operably associated with the retention frame itself or with the tube(s) defining the drug reservoir lumen and/or the retention frame lumen.

The retention frame lumen may be loaded with a retention frame (sometimes called a "wireform"), which may be an elastic wire. In one case, the retention frame includes a nitinol wire. The retention frame may be configured to spontaneously return to a retention shape, such as the illustrated "pretzel" shape or another coiled shape. For example, the retention frame may have an elastic limit and modulus that allows the device to be introduced into the body in a relatively lower-profile shape, permits the device to return to the relatively expanded shape once inside the body, and impedes the device from assuming the relatively lower-profile shape within the body in response to expected forces, such as the hydrodynamic forces associated with contraction of the detrusor muscle and urination. Thus, the device may be retained in the body once implanted, limiting or preventing accidental expulsion.

The material used to form the drug delivery device body may be elastic or flexible to permit moving the device between deployment and retention shapes. The material used to form the device body also may be water permeable or porous so that solubilizing fluid can enter the drug reservoir portion to solubilize the drug units once the device is implanted. For example, silicone or another biocompatible elastomeric material may be used.

In one embodiment in which the drug delivery device is designed to be implanted in the bladder, the drug delivery device is designed to be inserted into the bladder through the urethra cystoscopically. Thus, the device may be sized and shaped to fit through a narrow tubular path of a deployment instrument, such as a catheter or cystoscope. Typically, a cystoscope for an adult human has an outer diameter of about 5 to 7 mm and a working channel having an inner diameter of about 2.4 mm to about 2.6 mm. In other embodiments, a cystoscope has a working channel with a larger inner diameter, such as an inner diameter of 4 mm or more. Thus, the device may be relatively small in size. For example, when the device is elastically deformed to the relatively lower profile shape, the device for an adult patient may have a total outer diameter that is about 3.75 mm or less, such as about 2.6 mm or less. For pediatric patients, the dimensions of the device are anticipated to be smaller.

The overall shape of the intravesical device may enable the device to reorient itself within the bladder to reduce its engagement or contact with the bladder wall. The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder, as opposed to a particular bladder location located near the release orifice. However, devices that otherwise move freely within the bladder may be impeded from moving freely when the bladder is empty, and yet the device may still be tolerable if sufficiently compressible.

In some embodiments, the device is at least partially non-bioerodible. Suitable materials of construction may include medical grade silicone, natural latex, polytetrafluoroethylene (PTFE), expanded PTFE, poly(lactic-co-glycolic acid) (PLGA), poly(glycerol sebacate) (PGS), stainless steel, nitinol, elgiloy (non ferro magnetic metal alloy), polypropylene, polyethylene, polycarbonate, polyester, nylon, or combinations thereof. Following release of the drug formulation, the device and/or the retention frame may be removed substantially intact or in multiple pieces. In some embodiments, the device is partially bioerodible so that the device, upon partial erosion, breaks into non-erodible pieces small enough to be excreted from the bladder. Useful biocompatible erodible and non-erodible materials of construction are known in the art.

Generally, the drug delivery device includes at least one drug reservoir portion. In embodiments, the drug reservoir portion includes the part of the device body that forms at least one drug reservoir lumen, which houses a drug formulation of at least one drug. The drug reservoir portion may be bounded by a sidewall. The drug reservoir lumen may comprise an elastic tube, such as a polymeric tube. In one embodiment, the drug reservoir lumen of the device includes an elongated tube. An interior of the tube may define one or more drug reservoirs, and a drug formulation may be housed in the drug reservoir(s). In other embodiments, the drug reservoir lumen is in a form other than a tube.

The drug reservoir portion may operate as an osmotic pump. In such an embodiment, the tube may be formed from a water permeable material, such as a silicone, or tube may have a porous structure, or both. Following implantation, water or urine permeates through the wall of the tube, one or more apertures formed through the tube, or one or more passing pores formed through a porous tube. The water enters the reservoir, and is imbibed by the drug formulation. Solubilized drug is dispensed at a controlled rate out of the reservoir through the one or more apertures, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures; and the drug formulation dissolution profile, among other factors. The delivery rate can be predicted from the physicochemical parameters defining the particular drug delivery system, according to well known principles. In some embodiments, the device may initially exhibit a zero-order release rate and subsequently may exhibit a reduced, non-zero-order release rate, in which case the overall drug release profile may be determined by the initial zero-order release rate and the total payload.

In an alternative embodiment, the device may operate essentially by diffusion of the drug from the tube through (i) one or more discrete apertures formed in the wall of the tube, or passing pores formed in the wall of a porous tube, or (ii) through the wall of the tube itself, which may be permeable to the drug, or (iii) or through an end piece or wall disposed in one or both ends of the tube, or (iv) a combination thereof. In embodiments in which diffusion occurs through a wall, the apertures or passing pores may not be included. In still other embodiments, the device may operate by a combination of osmosis and diffusion.

The drug reservoir portion may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical implantation. In an embodiment, the drug reservoir portion is formed from a material that is both elastomeric and water permeable. One material that is both elastomeric and water permeable is silicone, although other biocompatible materials may be used.

The device body or a component thereof may be formed of a non-resorbable material. For example, it may be formed of a medical grade silicone tubing. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), PTFE and other fluorinated polymers, poly(siloxanes), copolymers thereof, and combinations thereof.

The device body or a component thereof may be bioerodible. It may be desirable to include a retrieval string even with a completely bioerodible device, for example, if the patient experiences unexpected side effects from the device or drug, then it may be desirable to remove the device earlier than the end of the treatment period. In embodiments, the device body, the bioerodible component used to confine the retrieval string, or both, may be made of a biodegradable or bioresorbable polymer. Examples of suitable such materials include synthetic polymers selected from poly(amides), poly(esters), poly(ester amides), poly(anhydrides), poly(orthoesters), polyphosphazenes, pseudo poly(amino acids), PGS, copolymers thereof, and mixtures thereof. In a preferred embodiment, the resorbable synthetic polymers are selected from poly(lactic acids), poly(glycolic acids), PLGA, poly(caprolactones), and mixtures thereof. Other curable bioresorbable elastomers include poly(caprolactone) (PC) derivatives, amino alcohol-based poly(ester amides) (PEA) and poly (octane-diol citrate) (POC).

The device body also may be configured to maintain the retention shape without, or at least without requiring, a retention frame. For example, the device body may include a "backbone" that holds the device in its retention shape. The "backbone" may be a thicker and/or stronger section of the material from which the drug reservoir portion is formed. The "backbone" may traverse the length of the drug reservoir portion, either linearly, spirally, or tortuously. In a particular embodiment, the device body is formed with a material that is treated or altered so that the device is deformable between a retention shape and a deployment shape. For example, the material used to form the drug reservoir portion may "memorize" and spontaneously assume the relatively expanded shape upon the application of heat to the device, such as when exposed to body temperatures upon entering the bladder. In some instances, the heating may cause at least a portion of the polymeric material to cross-link so that the device is capable of retaining the retention shape upon deployment in the bladder.

In some embodiments, the drug delivery device includes one or more apertures or orifices for dispensing the drug, such as via osmosis, diffusion, or a combination thereof, among other. The apertures may be spaced along the tube to provide a passageway for release of the drug formulation. The apertures or orifices may be positioned through a sidewall or an end of the tube.

The drug formulation can include essentially any therapeutic, prophylactic, or diagnostic agent, such as one that would be useful to release locally in/to the bladder or ureter for local or regionally treatments. The drug formulation may consist only of the drug, or one or more pharmaceutically acceptable excipients may be included. The drug may be a biologic. The drug may be a metabolite. As used herein, the term "drug" with reference to any specific drug described herein includes its alternative forms, such as salt forms, free acid forms, free base forms, solvates, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

The drug delivery device may be used to treat pain. A variety of anesthetic agents, analgesic agents, and combinations thereof may be used. The anesthetic agent may be a cocaine analogue. In particular embodiments, the anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with an anesthetic agent.

The analgesic agent may be an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

The analgesic agent may be a narcotic or non-narcotic agent. Representative examples of analgesics include acetaminophen, buprenorphine, butorphanol, codeine, dihydrocodeine, fentanyl, heroin, hydrocodone, hydromorphone, methadone, morphine, nicomorphine, oxycodone, oxymorphone, pentazocine, pethidine, propoxyphene, pyridium (phenazopyridine), thebaine, tramadol, alicyl alcohol, phenazopyridine hydrochloride, acetylsalicylic acid, flufenisal, ibuprofen, indoprofen, indomethacin, and naproxen. The analgesic agent may be selected, for example, from non-opioid, non-steroidal analgesics, opioid analgesics, and salicylates, among others types.

The drug delivery device may be used to treat inflammatory conditions such as IC/BPS (interstitial cystitis/bladder pain syndrome) as well as radiation cystitis, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones. Other examples of drugs that may be used in the treatment of IC/BPS include nerve growth factor monoclonal antibody (MAB) antagonists, such as Tanezumab, and calcium channel alpha-2-delta modulators, such as PD-299685 or gabepentin.

The drug delivery device may be used in association with the placement of a ureteral stent, such as to treat pain, urinary urgency or urinary frequency resulting from ureteral stent placement. Non-limiting examples of specific drugs for such treatment include antimuscarinics, α-blockers, narcotics, and phenazopyridine, among others.

The drug delivery device may be used to treat urinary incontinence, frequency, or urgency, including urge incontinence and neurogenic incontinence, as well as trigonitis. Drugs that may be used include anticholinergic agents, antispasmodic agents, antimuscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

The drug delivery device may be used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include *Bacillus* Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-a2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

The drug delivery device may be used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

The drug delivery device may be used to treat fibrosis of a genitourinary site, such as the bladder or uterus. Representative examples of drugs for the treatment of fibroids include pentoxphylline (xanthine analogue), antiTNF, anti-TGF agents, GnRH analogues, exogenous progestins, anti-progestins, selective estrogen receptor modulators, danazol and NSAIDs.

The drug delivery device may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

The drug may be selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinic agonist, choline ester).

In an embodiment, the drug formulation is in solid or semi-solid form, for example to reduce the overall volume of the drug formulation and thereby reduce the size of the device and/or to maintain the drug in a stable form during storage and before release. The semi-solid form may be, for example, an emulsion or suspension; a gel or a paste. The solid form may be solid drug units that are loaded into a drug reservoir (e.g., housing lumen). The drug unit is a solid, discrete object that substantially retains a selectively imparted shape (at the temperature and pressure conditions to which the delivery device normally will be exposed during assembly, storage, and handling before implantation). The drug units may be in the form of tablets, capsules, pellets, or beads, although other configurations are possible.

The present description is further illustrated by the following non-limiting example.

Example 1

Figure 13A:
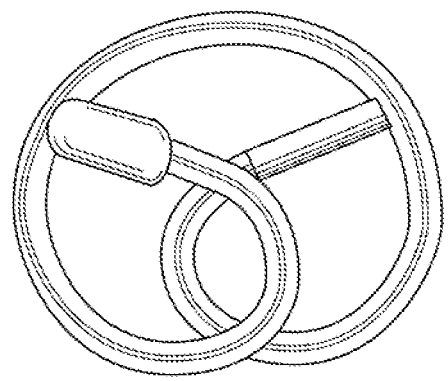
FIGS. 13A-B show a placebo drug delivery having a coiled retrieval string secured by a bioerodible cap. The device was built and tested in a simple in vitro voiding model, demonstrating controlled emergence of the retrieval string following degradation of the bioerodible cap.
Figure 13B:
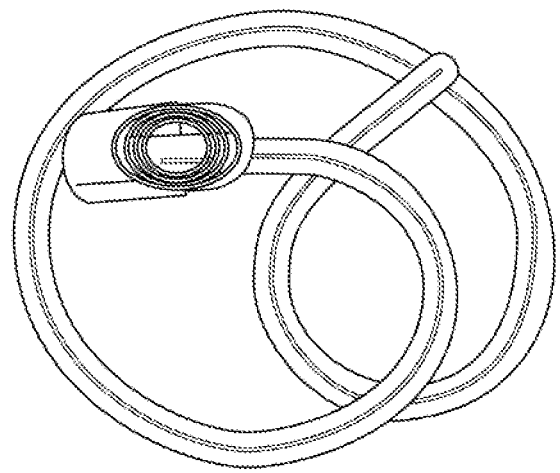
Figure 15:
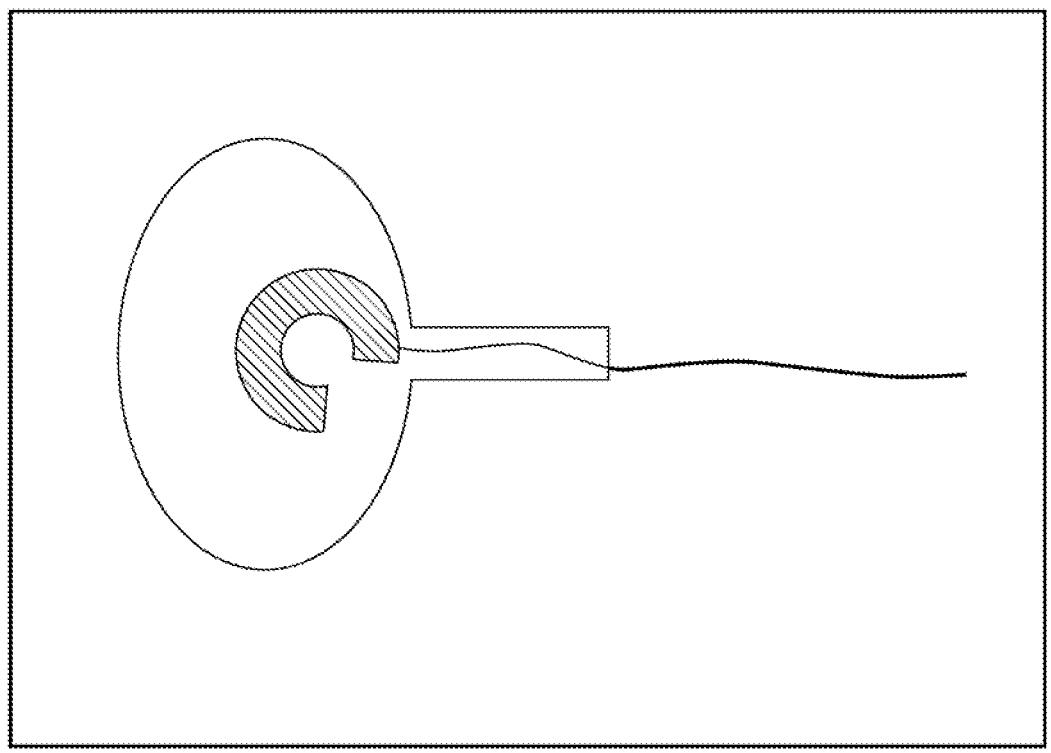
FIGS. 14-15 illustrate embodiments of an elongated, coiled or curved, intravesical drug delivery device, in which the retrieval string is attached in a middle portion of the device or to an end of the device.

ETHIBOND EXCEL™ (Ethicon Endo-Surgery Inc.) polyester suture (size 5-0, green braided) was used as a retrieval string. A placebo drug delivery device (silicone tube with pretzel-shaped retention frame) was used as a representative urological device. One end of the retrieval string was attached to an end of the device. Then, the string was spirally wound or coiled and was collapsed so that it could be confined to a plane (FIGS. 13A and 13B). Then, a biodegradable cap was placed over the bundled string. Specifically, a gelatin capsule cap (size 4) was used as shown in FIGS. 13A and 13B, although other degradable polymers, such as PLGA could have been used.

A simple voiding model, which consisted of a funnel (16 oz capacity) and latex tubing (ID: 6.35 mm and length: 23 cm) was used as a test apparatus. The drug delivery device with capped/confined retrieval string was placed inside the funnel part and water was filled while one end of the latex tubing was clamped. The tubing was unclamped when the funnel was emptied so that the funnel was emptied only by gravity. As the gelatin cap dissolved, the bunched string was unwound in the water. After repeating the filling and emptying steps several times, the retrieval string emerged at the end of the tubing. Thus, this experiment demonstrated controlled emergence of the retrieval string.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A medical device, comprising:
   a urological device; and
   at least one retrieval string attached to the urological device at an attachment position, the at least one retrieval string having a proximal end connected to the urological device and an opposed distal end,
   wherein the at least one retrieval string is configured in an initial confined form, in which the at least one retrieval string is confined in or on the urological device, which, following deployment of the medical device in a urinary bladder of a patient, changes to an unconfined form in which the distal end of the at least one retrieval string is extendible into the urethra of the bladder, the device thereby providing controlled emergence of the distal end of the at least one retrieval string from the urethra to enable extraction of the medical device from the bladder by pulling the at least one retrieval string,
   wherein the controlled emergence of the distal end of the at least one retrieval string occurs without manual manipulation of the at least one retrieval string, and
   wherein the distal end of the at least one retrieval string in the initial confined form is fixed relative to the attachment position and at a position closer to the attachment position than its position when the at least one retrieval string is in the unconfined form.

2. The medical device of claim 1, further comprising at least one bioerodible component operable to (i) maintain the at least one retrieval string in the initial confined form, and (ii) permit the at least one retrieval string to take the unconfined form following degradation of the at least one bioerodible component in vivo.

3. The medical device of claim 2, further comprising a hydrodynamic cap which is attached to the urological device via the at least one bioerodible component, the hydrodynamic cap being configured to advance through the urethra when exposed to hydrodynamic forces during urination, to provide the controlled emergence of the retrieval string from the urethra.

4. The medical device of claim 2, wherein the at least one bioerodible component contains at least a portion of the at least one retrieval string in the initial confined form.

5. The medical device of claim 2, wherein the at least one bioerodible component comprises a plurality of bands wrapped around the urological device and securing the at least one retrieval string onto an outer surface of the urological device.

6. The medical device of claim 5, wherein the at least one retrieval string is a monofilament.

7. The medical device of claim 1, wherein at least part of the at least one retrieval string in the initial confined form is coiled.

8. The medical device of claim 7, wherein the coiled retrieval string comprises a water-soluble adhesive coating.

9. The medical device of claim 7, wherein the at least one retrieval string is composed of silk or a braided polyester.

10. The medical device of claim 1, wherein the urological device comprises an intravesical drug delivery device, and wherein the at least one retrieval string is configured to change to the unconfined form following release of a drug from the drug delivery device.

11. The medical device of claim 1, wherein the urological device comprises a ureteral stent.

12. The medical device of claim 1, wherein the urological device comprises (i) a device body having at least one drug reservoir lumen, and (ii) a drug formulation positioned in the at least one drug reservoir lumen, wherein the urological device is elastically deformable between a retention shape for retaining the urological device in the bladder and a low profile shape for deployment of the urological device through the patient's urethra.

13. The medical device of claim 12, wherein the urological device is configured to permit the distal end of the at least one retrieval string in the unconfined form to extend out from the urethra of the bladder when the urological device is in the retention shape and thereby enable the patient or a physician to pull the distal end of the at least one retrieval string and cause the urological device to take the low profile shape, permitting the urological device to be extracted through the patient's urethra.

14. A method of removing a urological device from a patient comprising:
   grasping the at least one retrieval string of the medical device of claim 1 deployed in the urinary bladder of the patient; and
   pulling the at least one retrieval string and the attached urological device through and out of the urethra of the patient.

15. The method of claim 14, wherein the grasping step comprises grasping the distal end portion of the at least one retrieval string which extends from the patient's urethra.

16. The medical device of claim 1, wherein:
   the urological device is an intravesical drug delivery device comprising a drug reservoir lumen which houses a drug formulation; and
   the medical device further comprises a bioerodible component operable to (i) maintain the retrieval string in the initial confined form, and (ii) permit the retrieval string to take the unconfined form and extend from the patient's urethra following in vivo degradation of the bioerodible component after the drug formulation is substantially or completely released.

17. The medical device of claim 1, wherein the at least one retrieval string is wound, coiled, encapsulated in or on the urological device in the initial confined form.

18. A medical device, comprising:
- a urological device comprising an intravesical drug delivery device; and
- a retrieval string attached to the urological device, the retrieval string having a proximal end connected to the urological device and an opposed distal end,
- wherein a string body of the retrieval string comprises a ferromagnetic material at least along a length of the string body to permit magnetically manipulating the retrieval string through the urethra to enable extraction of the medical device, and
- wherein the urological device is configured for deployment wholly in a urinary bladder of a patient, prior to retrieval.

19. The medical device of claim 18, wherein the string body of the retrieval string is hollow and the ferromagnetic material is contained in a lumen of the retrieval string.

20. The medical device of claim 18, wherein the string body of the retrieval string is solid and the ferromagnetic material is embedded in the string body of the retrieval string.

21. The medical device of claim 18, wherein the ferromagnetic material is disposed on an outer surface of the string body of the retrieval string.

22. The medical device of claim 18, wherein the retrieval string is buoyant in urine.

23. The medical device of claim 18, wherein the intravesical drug delivery device comprises (i) a device body having at least one drug reservoir lumen, and (ii) a drug formulation positioned in the at least one drug reservoir lumen, wherein the device is elastically deformable between a retention shape for retaining the urological device in a bladder and a low profile shape for deployment of the urological device through a patient's urethra.

24. The medical device of claim 23, wherein the retrieval string is buoyant in urine.

25. A method of removing a urological device from a patient comprising:
- grasping the at least one retrieval string of the medical device of claim 18 deployed in the patient; and
- pulling the at least one retrieval string and the attached urological device through and out of the urethra of the patient.

26. The method of claim 25, wherein the grasping comprises magnetically coupling a distal end of a urethrally-inserted catheter to the at least one retrieval string.

27. A medical device, comprising:
- a urological device; and
- a retrieval string attached to the urological device, the retrieval string having a proximal end connected the urological device and an opposed distal end,
- wherein the retrieval string comprises a hydrodynamic cap connected to the distal end, the hydrodynamic cap being configured to advance through the urethra when exposed to hydrodynamic forces during urination, to provide controlled emergence of the retrieval string from the urethra to enable extraction of the urological device by pulling the at least one retrieval string.

28. The medical device of claim 27, wherein the retrieval string and the hydrodynamic cap are non-buoyant in urine.

* * * * *

UNITED STATES PATENT AND TRADEMARK OFFICE
CERTIFICATE OF CORRECTION

PATENT NO. : 10,857,336 B2  
APPLICATION NO. : 14/397401  
DATED : December 8, 2020  
INVENTOR(S) : Lee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1056 days.

Signed and Sealed this  
Sixth Day of December, 2022

Katherine Kelly Vidal  
*Director of the United States Patent and Trademark Office*